United States Patent
Geiser et al.

(10) Patent No.: US 7,867,271 B2
(45) Date of Patent: Jan. 11, 2011

(54) RAPID-EXCHANGE DELIVERY SYSTEMS FOR SELF-EXPANDING STENTS

(75) Inventors: Timothy A. Geiser, Temecula, CA (US); Charles R. Peterson, Murrieta, CA (US); Andy Denison, Temecula, CA (US); Stephanie Klocke, Mountain View, CA (US); Samir Patel, Mountain View, CA (US); Joanna Lubas, Fremont, CA (US); Joanne Lumauig, San Jose, CA (US); Kathy Lind, Temecula, CA (US); Keif Fitzgerald, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1166 days.

(21) Appl. No.: 10/720,032

(22) Filed: Nov. 20, 2003

(65) Prior Publication Data
US 2005/0113902 A1    May 26, 2005

(51) Int. Cl.
*A61F 2/06* (2006.01)
(52) U.S. Cl. .................................... 623/1.12
(58) Field of Classification Search ................ 623/1.11, 623/1.12; 604/103.04, 103.05; 606/108, 606/200, 119, 194–198; 128/897–899
See application file for complete search history.

(56) References Cited

U.S. PATENT DOCUMENTS

| | | | |
|---|---|---|---|
| 3,856,190 A | 12/1974 | Mole et al. | |
| 3,880,483 A | 4/1975 | Snyder, Jr. | |
| 4,748,982 A | 6/1988 | Horzewski et al. | |
| 5,061,273 A | 10/1991 | Yock | |
| 5,147,379 A | 9/1992 | Sabbaghian et al. | |
| 5,156,594 A | 10/1992 | Keith | |
| 5,176,661 A | 1/1993 | Evard et al. | |
| 5,180,368 A | 1/1993 | Garrison | |
| 5,195,978 A | 3/1993 | Schiffer | |
| 5,279,562 A | 1/1994 | Sirhan et al. | |
| 5,300,085 A | 4/1994 | Yock | |
| 5,346,505 A | 9/1994 | Leopold | |
| 5,360,401 A | 11/1994 | Turnland | |
| 5,389,087 A | 2/1995 | Miraki | |
| 5,443,457 A | 8/1995 | Ginn et al. | |

(Continued)

FOREIGN PATENT DOCUMENTS

EP    0 819 411 A2    1/1998

(Continued)

*Primary Examiner*—Anhtuan T Nguyen
*Assistant Examiner*—Elizabeth Houston
(74) *Attorney, Agent, or Firm*—Fulwider Patton LLP; Abbott Vascular; Jonathan Feuchtwang

(57) ABSTRACT

A catheter assembly is provided having an inner member and an outer member extending along a longitudinal axis, the inner member and the outer member having a coaxial configuration and dimensioned for relative axial movement. The outer member may include an anti rotation member adapted to engage with a longitudinal slot formed on the inner member so as to maintain rotational alignment between inner member and outer member. The inner member can be made with a proximal portion made from a tubing such as hypotubing or a coil tubing. The inner member also may be made with a proximal portion made with a support mandrel. A coil tubing can be utilized to form the guide wire receiving member which is attached to the inner member.

35 Claims, 10 Drawing Sheets

U.S. PATENT DOCUMENTS

| | | | |
|---|---|---|---|
| 5,458,613 A | 10/1995 | Gharibadeh et al. | |
| 5,516,336 A | 5/1996 | McInnes et al. | |
| 5,533,968 A | 7/1996 | Muni et al. | |
| 5,545,134 A | 8/1996 | Hilaire et al. | |
| 5,545,138 A * | 8/1996 | Fugoso et al. | 604/103.1 |
| 5,567,203 A | 10/1996 | Euteneuer et al. | |
| 5,571,094 A | 11/1996 | Sirhan | |
| 5,656,013 A | 8/1997 | Yoon | |
| 5,690,644 A | 11/1997 | Yurek et al. | |
| 5,743,874 A * | 4/1998 | Fischell et al. | 604/103.1 |
| 5,743,875 A | 4/1998 | Sirhan et al. | |
| 5,792,144 A | 8/1998 | Fischell et al. | |
| 5,807,355 A | 9/1998 | Ramzipoor et al. | |
| 5,823,995 A | 10/1998 | Fitzmaurice et al. | |
| 5,935,114 A | 8/1999 | Jang et al. | |
| 5,951,569 A | 9/1999 | Tuckey et al. | |
| 5,993,460 A | 11/1999 | Beitelia et al. | |
| 6,007,522 A | 12/1999 | Agro et al. | |
| 6,019,778 A * | 2/2000 | Wilson et al. | 606/198 |
| 6,045,570 A | 4/2000 | Epstein et al. | |
| 6,077,295 A | 6/2000 | Limon et al. | |
| 6,132,389 A | 10/2000 | Cornish et al. | |
| 6,143,021 A | 11/2000 | Stachle | |
| 6,165,167 A | 12/2000 | Delaloye | |
| 6,174,316 B1 | 1/2001 | Tuckey et al. | |
| 6,179,810 B1 | 1/2001 | Wantink et al. | |
| 6,190,358 B1 | 2/2001 | Fitzmaurice et al. | |
| 6,193,686 B1 | 2/2001 | Estrada et al. | |
| 6,248,122 B1 | 6/2001 | Klumb et al. | |
| 6,254,609 B1 * | 7/2001 | Vrba et al. | 606/108 |
| 6,273,899 B1 | 8/2001 | Kramer | |
| 6,287,329 B1 * | 9/2001 | Duerig et al. | 623/1.11 |
| 6,290,673 B1 | 9/2001 | Shanley | |
| 6,299,595 B1 | 10/2001 | Dutta et al. | |
| 6,375,676 B1 | 4/2002 | Cox | |
| 6,380,457 B1 * | 4/2002 | Yurek et al. | 623/1.11 |
| 6,475,187 B1 | 11/2002 | Gerberding | |
| 6,514,261 B1 | 2/2003 | Randall et al. | |
| 6,520,983 B1 | 2/2003 | Colgan et al. | |
| 6,589,207 B1 * | 7/2003 | El-Nounou | 604/103.04 |
| 6,679,909 B2 | 1/2004 | McIntosh et al. | |
| 6,736,839 B2 * | 5/2004 | Cummings | 623/1.11 |
| 6,755,855 B2 | 6/2004 | Yurek et al. | |
| 7,122,050 B2 | 10/2006 | Randall et al. | |
| 2002/0082548 A1 | 6/2002 | Sanchez et al. | |
| 2003/0028235 A1 * | 2/2003 | McIntosh et al. | 623/1.11 |
| 2003/0199821 A1 | 10/2003 | Yurek et al. | |

FOREIGN PATENT DOCUMENTS

| | | |
|---|---|---|
| EP | 1 095 634 A2 | 5/2001 |
| WO | WO 01/43664 A1 | 6/2001 |
| WO | WO 03/002020 | 1/2003 |

* cited by examiner

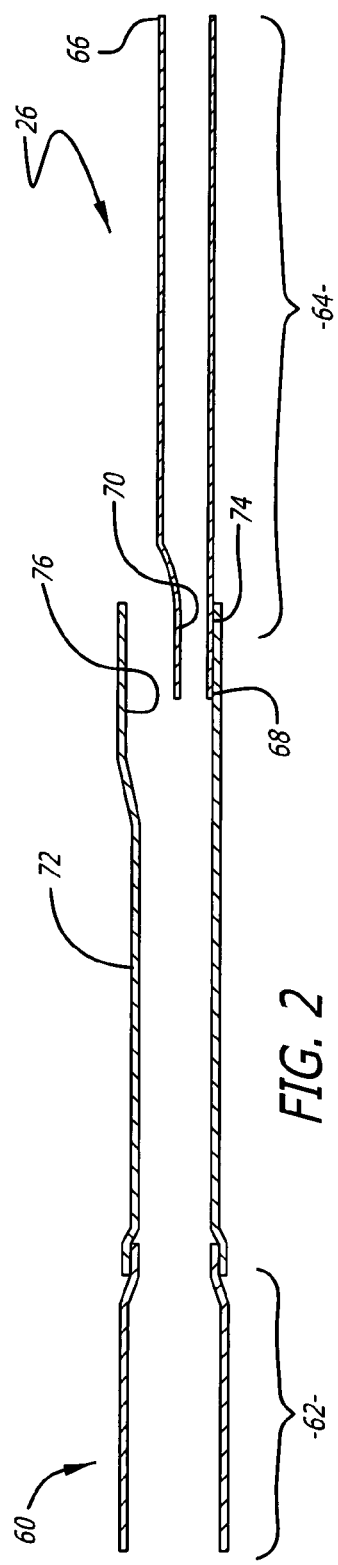
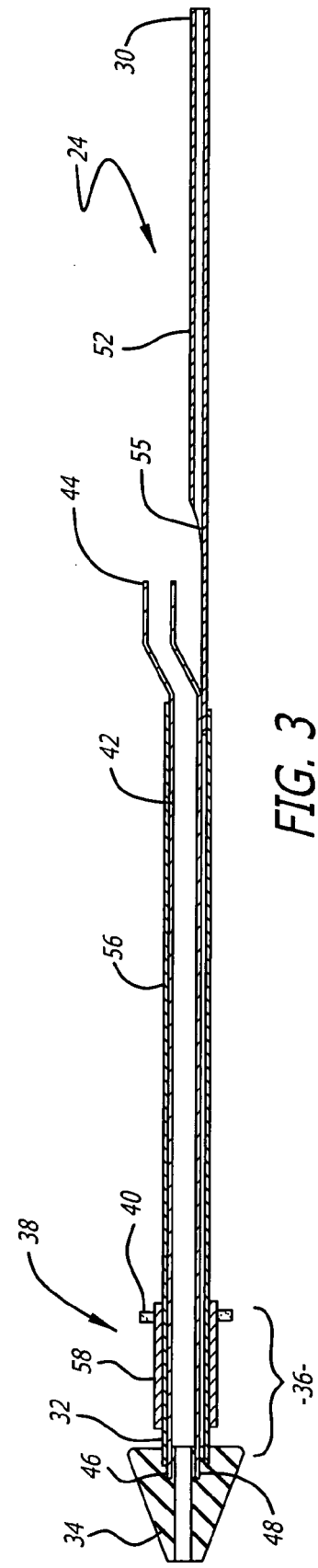
FIG. 2
FIG. 3

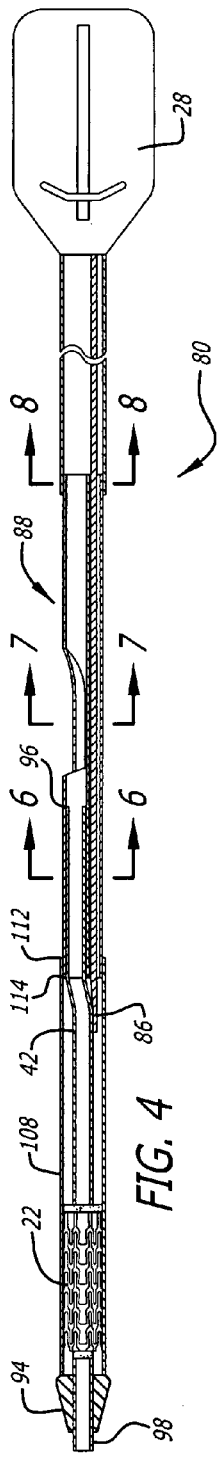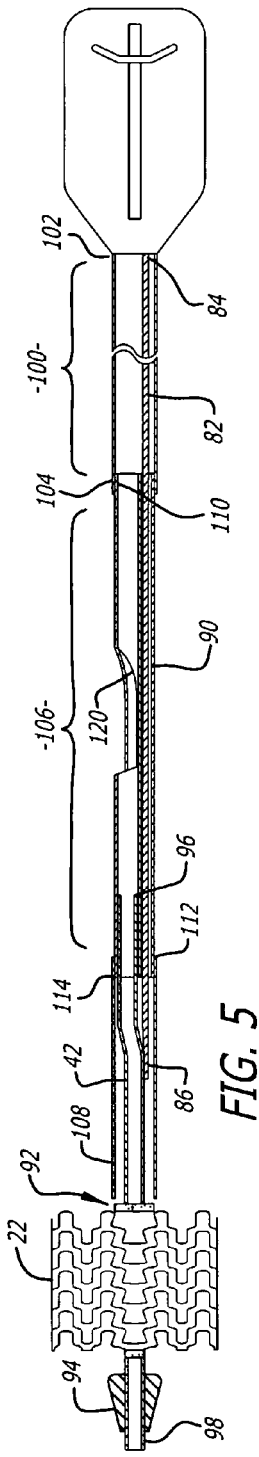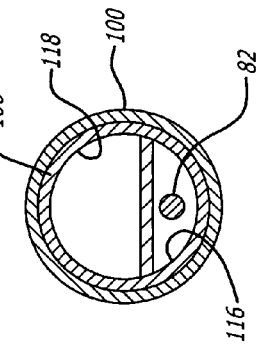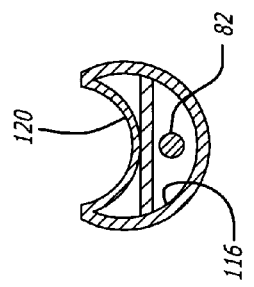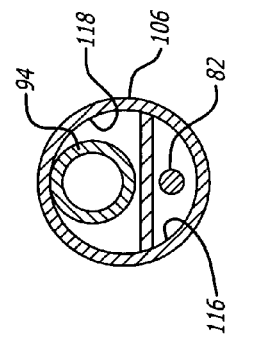
FIG. 4
FIG. 5
FIG. 6
FIG. 7
FIG. 8

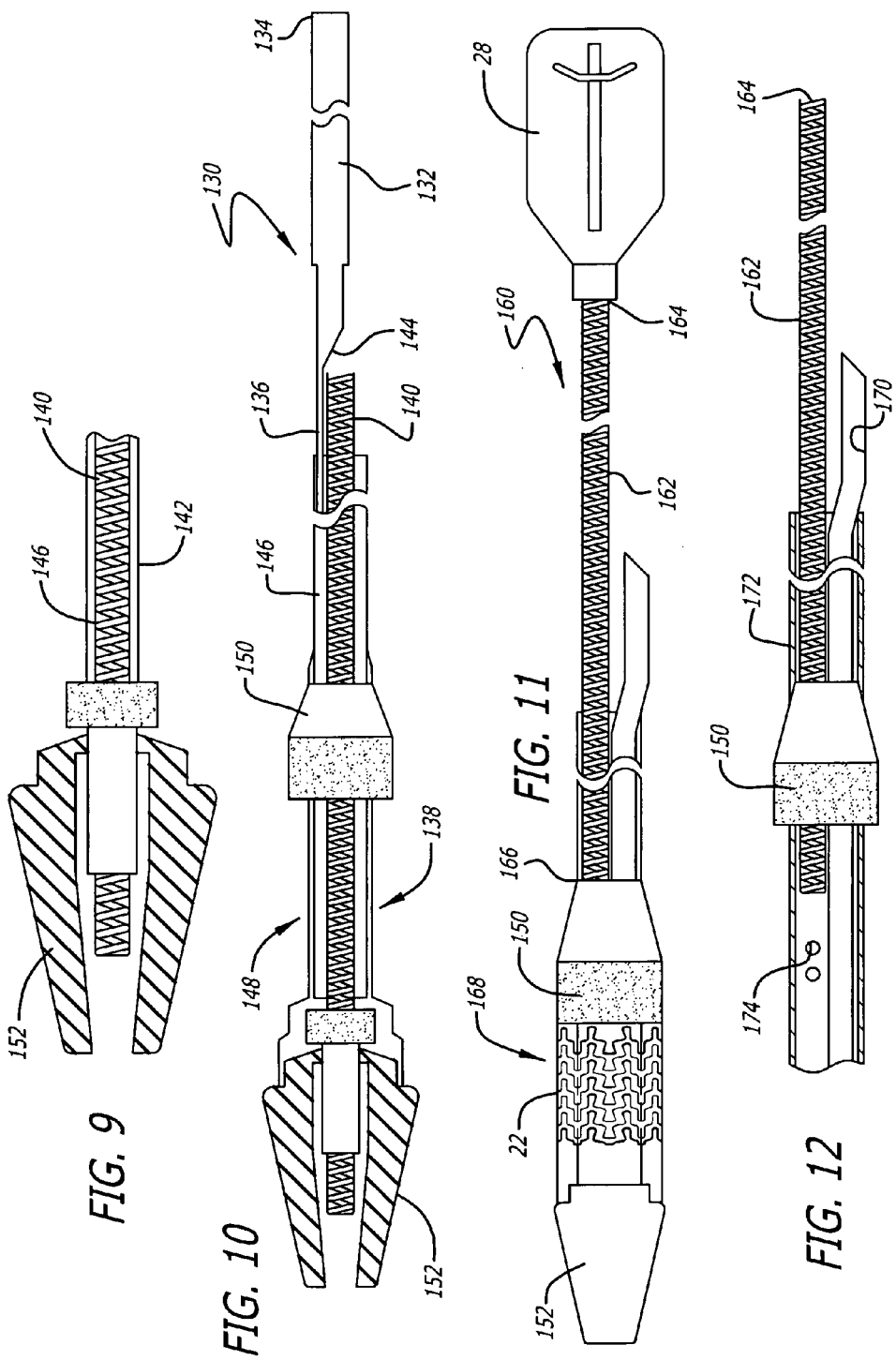

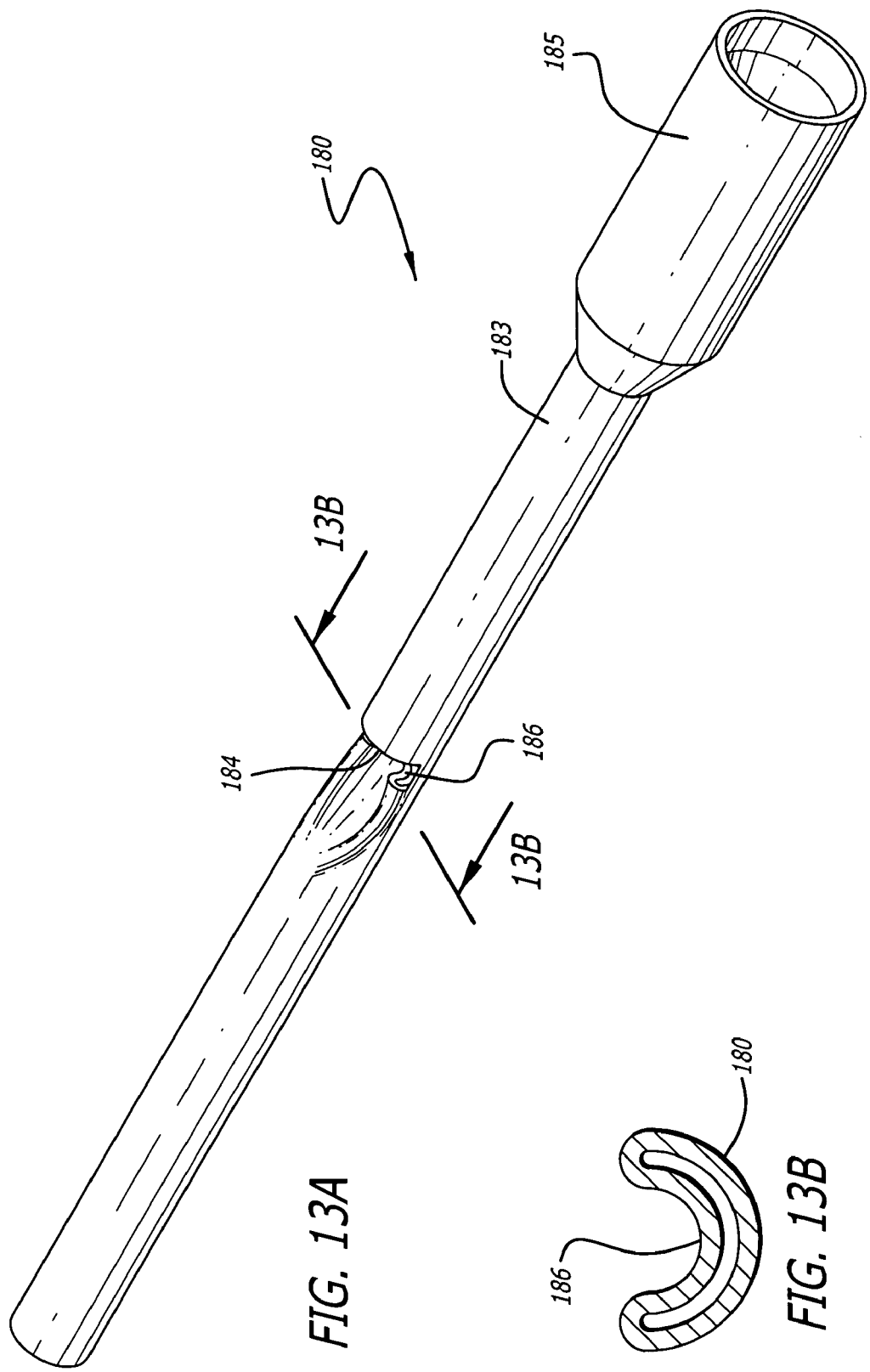

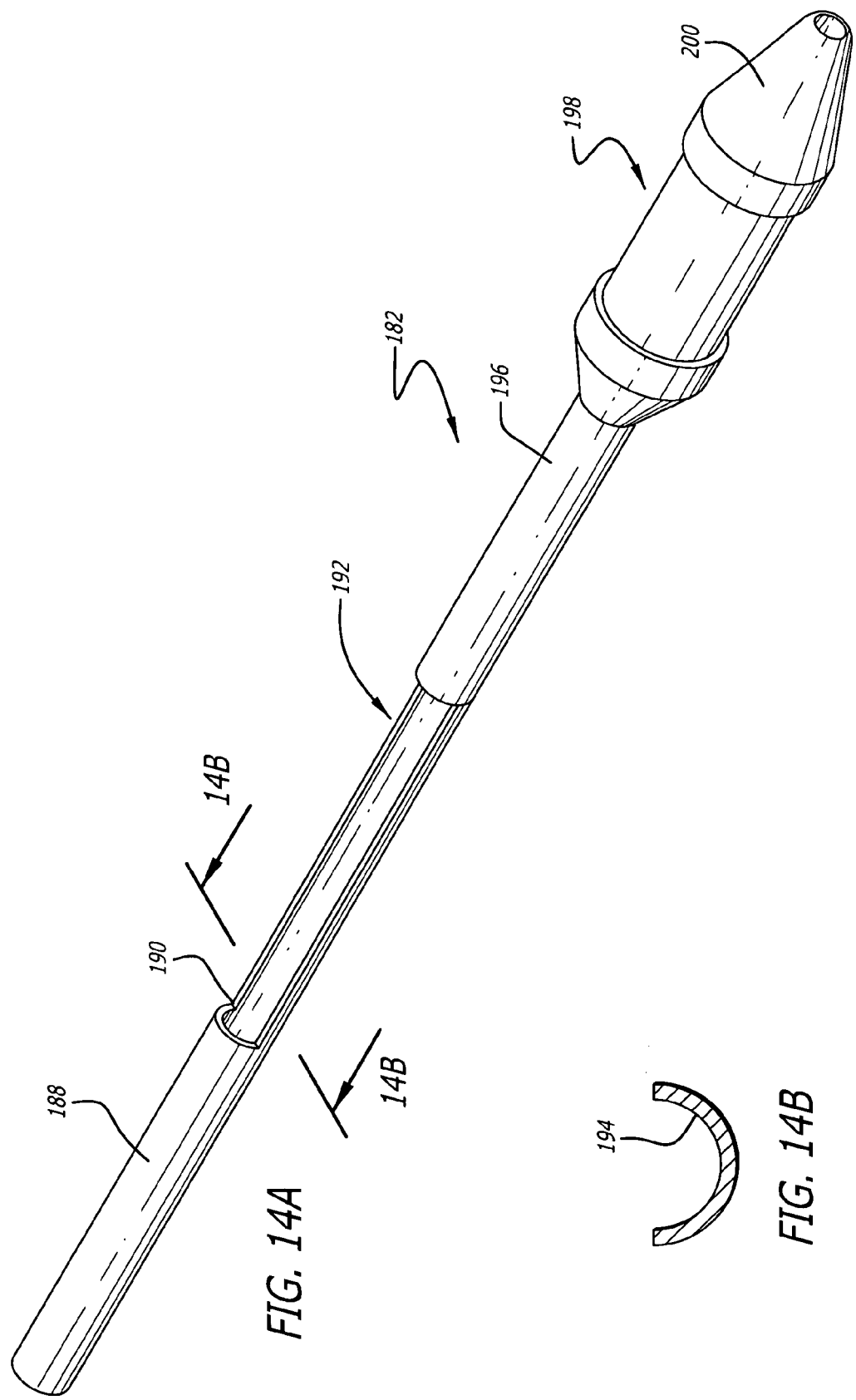

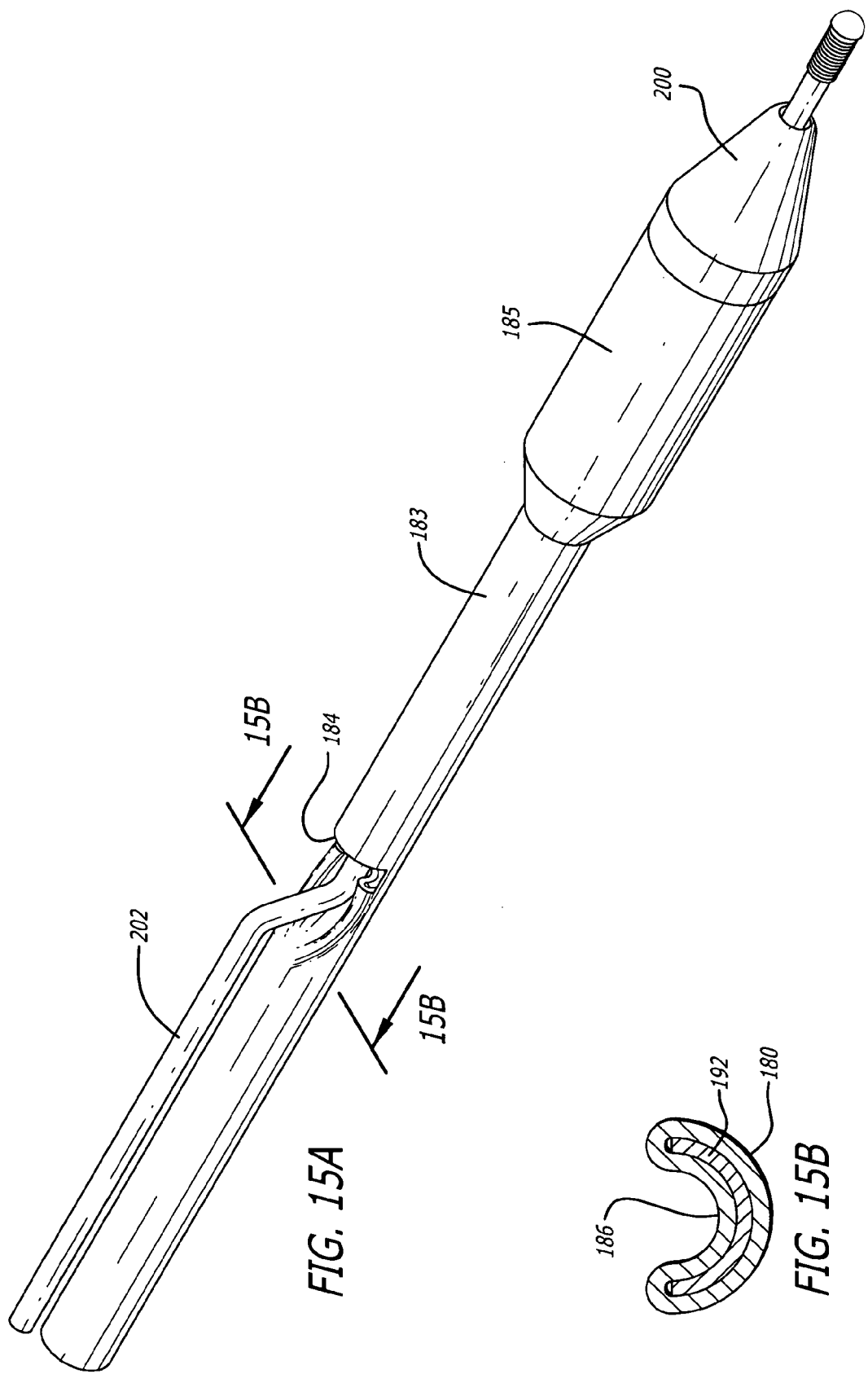

RAPID-EXCHANGE DELIVERY SYSTEMS FOR SELF-EXPANDING STENTS

BACKGROUND OF THE INVENTION

The invention relates to stent delivery systems, which are used to implant a stent into a patient's body lumen to maintain the patency thereof. The stent delivery system is useful in the treatment and repair of body lumens, including coronary arteries, renal arteries, carotid arteries, and other body lumens.

Stents are generally cylindrically-shaped devices which function to hold open and sometimes expand a segment of a blood vessel or other body lumen. They are particularly suitable for use to support and hold back a dissected arterial lining which can occlude the fluid passageway therethrough. Stents also are useful in maintaining the patency of a body lumen, such as a coronary artery, after a percutaneous transluminal coronary angioplasty (PTCA) procedure or an atherectomy procedure to open a stenosed area of the artery.

Typically, a stent is delivered intraluminally through a percutaneous incision through the femoral or renal arteries. The stent is mounted on the distal end of an elongated catheter and the catheter and stent are advanced intraluminally to the site where the stent is to be implanted. A variety of devices are known in the art for use as stents and have included coiled wires in a variety of patterns that are expanded after being placed intraluminally. Three different approaches for expanding stents have been developed in the art, namely, balloon expanded stents, elastically self-expanding stents, and heat expanded stents. Balloon expanded stents are placed over a deflated balloon mounted on the catheter. The balloon is then inflated to expand the stent radially outwardly into contact with the arterial wall, whereupon the stent undergoes plastic deformation and remains in an expanded state to hold open and support the artery. Elastically self-expanding stents are adapted to be delivered in an elastically compressed state while confined within an outer restraining sheath, but to elastically expand when the sheath is removed and to provide support to the vessel within which it is implanted. Heat expanded stents are made from heat-sensitive materials such as nickel-titanium, are cooled in a compressed shape before insertion into the patient, but assume a pre-existing expanded shape when exposed to the body temperature of a patient.

With respect to self-expanding stents, typically a retractable sheath is positioned over the self-expanding stent which is mounted on the distal end of the catheter. Once the catheter has been advanced intraluminally to the site where the stent is to be implanted, the sheath is withdrawn thereby allowing the self-expanding stent to expand radially outwardly into contact with the arterial wall, thereby holding open and supporting the artery. Both balloon expanded stents and heat sensitive self-expanding stents may also be delivered within a retractable sheath, similar to that used with a self-expanding stent. In such cases the sheath may function to secure the stent on the catheter during insertion or to prevent sharp edges of the stent from tearing at the wall of the lumen during insertion.

One embodiment of a catheter delivery system is the so-called "over-the-wire" delivery system, in which a catheter is introduced into the patient over a guide wire which has been previously introduced. In this embodiment, the guide wire runs within a lumen extending the entire length of the catheter. Another embodiment of the catheter delivery system is the so-called "rapid-exchange" delivery system, in which the guide wire runs within a lumen in the catheter extending from the distal tip of the catheter to a point just proximal of where the stent is positioned on the catheter, at which point the lumen terminates on the outside of the catheter and the guide wire emerges from the catheter to extend proximally, outside of the catheter. Thus, the catheter of a "rapid-exchange" delivery system has a guide wire lumen port at the distal end of the catheter, and a proximal port spaced a relatively short distance from the distal end and a relatively long distance from the proximal end of the catheter. This "rapid-exchange" configuration allows the surgeon to rapidly and single-handedly place the delivery system over the guide wire or to exchange one delivery system for another, because the length of the guide wire lumen in the catheter is much shorter than that used in an over-the-wire delivery system.

One of the problems associated with the prior art catheter-delivery systems which use a retractable outer sheath is that the addition of a retractable sheath tends to reduce the overall flexibility of the delivery system. However, there is still a need to maintain a low-profile in the distal region of the catheter delivery system in order to track the sometimes tortuous anatomy to deliver the stent to the target area. In this regard, catheter delivery systems still need to utilize a catheter, upon which the self-expanding stent is mounted, that provide a rigid column to allow the physician to push the entire catheter over the pre-deployed guide wire to reach the target area. This stent-mounted catheter also must have sufficient strength to prevent compression or tensile forces from acting on the catheter as it is being delivered over the guide wire. In this regard, the stent-mounted catheter must be able to slide forward and backwards without tangling, kinking or adversely affecting the deployment of the stent.

Another problem that exists in the case of the rapid-exchange delivery system is that the addition of a retractable sheath to surround the catheter introduces a problem of rotational alignment between the sheath and the catheter. Upon commencement of installing the delivery system over the guide wire, the surgeon must introduce the proximal tip of the guide wire into the catheter lumen at the distal tip of the catheter. The surgeon then advances the guide wire proximally through the catheter lumen until the proximal tip of the guide wire emerges from the catheter and protrudes through an opening in the wall of the sheath. If, during the foregoing process, the sheath rotates relative to the catheter, the surgeon may have difficulty in aligning the opening with the guide wire tip, so as to get the guide wire tip to protrude from the opening. This complication can be a major problem for the surgeon to resolve under the pressure of surgery.

Thus, there has been found a need for a reliable rapid-exchange stent delivery system for a self-expanding stent, in which the stent-mounted catheter maintains a low-profile, yet is able to move axially along the deployed guide wire without tangling, kinking or adversely affecting the deployment of the stent. Moreover, there is a need for a reliable rapid-exchange stent delivery system in which rotational alignment between the outer sheath and the catheter may be maintained prior to, and during, the process of positioning the delivery system over the guide wire. Further, the art has found a need for a delivery system for a self-expanding stent which has improved flexibility characteristics. The present invention addresses these and other needs.

SUMMARY OF THE INVENTION

The present invention is directed to a catheter delivery system having improved flexibility characteristics. In one aspect, the invention is directed to a rapid-exchange catheter delivery system having an outer member including a restraining sheath portion, in which the sheath is held in rotational alignment with the catheter prior to and during the process of positioning the delivery system over a guide wire. Means for maintaining such rotational alignment may assume the form of a U-shaped member or a tab-like member formed on the outer member of the catheter assembly and adapted to protrude through a slot or opening defined in the stent-mounted portion of the catheter.

A catheter assembly for removably attaching an intravascular stent is provided in which an elongated catheter includes an inner member and an outer member extending along a longitudinal axis, wherein the inner member and the outer member are dimensioned for relative axial movement. A self-expanding stent, having an open lattice structure, and being adapted to be expandable to an open configuration, is mounted on the inner member and restrained by the outer member.

In one particular aspect of the present invention, the inner member of the composite rapid-exchange catheter assembly includes a proximal portion made from a hypotube which minimizes the chance of compression or tensile forces acting on the catheter assembly. The hypotube also provides a channel for flushing the system with a fluid, such as saline, prior to usage. In this manner, the inner member provides a conduit for helping evacuate air bubbles from the catheter assembly prior to usage. In one particular embodiment of the invention, the proximal portion of the inner member can be made from polymeric coated coil tubing which is utilized to help prevent compression of the inner member without decreasing the flexibility of the rapid-exchange delivery system. Such a tubing also could be used in an over-the-wire stent delivery system. In yet another aspect of the invention, the polymeric coated coil tubing could be utilized as the guide wire receiving member for a rapid-exchange version of the self-expanding stent system. The use of this polymeric coated coil tubing should not reduce the flexibility or trackability of the catheter during usage, but should prevent compression or kinking when being deployed.

The present invention includes an anti-rotation member formed on the outer member which is adjacent to the guide wire exit opening. In one particular form of the invention, the anti-rotation member takes on a U-shape or, alternatively, a tab-like member formed on the outer member which engages a similarly shaped lumen formed on the inner member so as to maintain the inner member and the outer member in rotational alignment. It should be appreciated that the shape in which the anti-rotation member is formed can be any one of a number of geometric shapes, including a square, V-shape, and the like. Accordingly, the lumen formed on the inner member would be similarly shaped to fit within the particular shape of the anti-rotation member. The anti-rotation member is adapted to extend radially inwardly and to engage the particular shaped slot in the inner member to allow the inner member and outer member to move axially relative to each other while preventing rotational motion between these components. A guide wire notch and exit opening extend through a slot in the outer member and through the slot in the inner member to create a rapid-exchange system. Axial motion between the inner member and outer member does not interfere with the positioning of the guide wire within the guide wire notch.

In another aspect of the present invention, the distal portion of the outer member which forms the restraining sheath portion of the self-expanding stent delivery system can be made from a Nylon-coated polyimide material that provides high-strength tubing with a low-wall thickness. Such a material can resist an equal amount of hoop stress at a much lower wall thickness than with a Nylon material alone. In one component, a Nylon material is bonded to the outside of a polyimide tubing. The inner surface of the polyimide tubing remains resistant to stent-strut indentation caused by the outward radial force exerted by the collapsed self-expanding stent. The Nylon material bonded to the outside of the sheath portion provides the necessary tubing strength to restrain the stent in a collapsed delivery position, but with a lower wall thickness. As a result, the profile of the stent delivery system can be reduced at its distal region by utilizing such a composite material.

Other features and advantages of the present invention will become more apparent from the following detailed description of the invention, when taken in conjunction with the accompanying exemplary drawings.

BRIEF DESCRIPTION OF THE DRAWINGS

FIG. 2 is a side elevational view, partially in cross section, showing the outer member which forms part of the rapid-exchange stent delivery system of FIG. 1.

FIG. 3 is a side elevational view, partially in cross section, showing the inner member which forms part of the rapid-exchange stent delivery system of FIG. 1.

FIG. 4 is a side elevational view, partially in cross section, showing an alternative embodiment of a rapid-exchange stent delivery system embodying features of the present invention.

FIG. 5 is a side elevational view, partially in cross section, showing the rapid-exchange stent delivery system of FIG. 4 in a post-deployment position.

FIG. 6 is cross sectional view taken along line 6-6 of FIG. 4.

FIG. 7 is a cross sectional view taken along line 7-7 of FIG. 4.

FIG. 8 is a cross sectional view taken along line 8-8 of FIG. 4.

FIG. 9 is a side elevational view, partially in cross section, showing an alternative embodiment of the distal portion of an inner member which can be utilized in accordance with a rapid-exchange stent delivery system incorporating features of the present invention.

FIG. 10 is a side elevational view, partially in cross section, showing an alternative embodiment of an inner member assembly which includes the coil guide wire receiving member depicted in FIG. 9.

FIG. 11 is a side elevational view, partially in cross section, showing an alternative embodiment of inner member which can be used in accordance with a rapid-exchange stent delivery system embodying features of the present invention.

FIG. 12 is a side elevational view, partially in cross section, showing the assembly of the inner member which forms part of the a rapid-exchange stent delivery system of FIG. 11.

FIG. 13A is a perspective view showing an alternative embodiment of a distal portion of an outer member which forms part of a rapid-exchange stent delivery system embodying features of the present invention.

FIG. 13B is a cross sectional view taken along line 13B-13B of FIG. 13A.

FIG. 14A is a perspective view showing an alternative embodiment of a distal portion of an inner member assembly which forms part of a rapid-exchange stent delivery system embodying features of the present invention.

FIG. 14B is a cross sectional view taken along line 14B-14B of FIG. 14A.

FIG. 15A is a perspective view showing the complete distal junction assembly, which includes the outer member of FIG. 13A and the inner member of FIG. 14A.

FIG. 15B is cross sectional view taken along lines 15B-15B of FIG. 15A.

DETAILED DESCRIPTION OF THE PREFERRED EMBODIMENTS

The present invention relates to rapid-exchange delivery catheter systems in which a stent is delivered intraluminally into a human patient's body lumen, such as a coronary artery, carotid artery, renal artery, peripheral artery and veins, and the like, and implanted therein.

There are numerous prior art stent delivery systems which may be used in conjunction with the present invention. The stent delivery systems suitable for use with the present invention are "rapid-exchange" delivery systems which have an outer sheath adapted to slide over an inner catheter so as to cover a stent. The invention described in detail herein is described in the context of an elastically self-expanding stent delivery system. However, the invention is not limited to such use, and may equally be used with a delivery system for a balloon expanded stent or heat-expanded stent.

Figure 1:
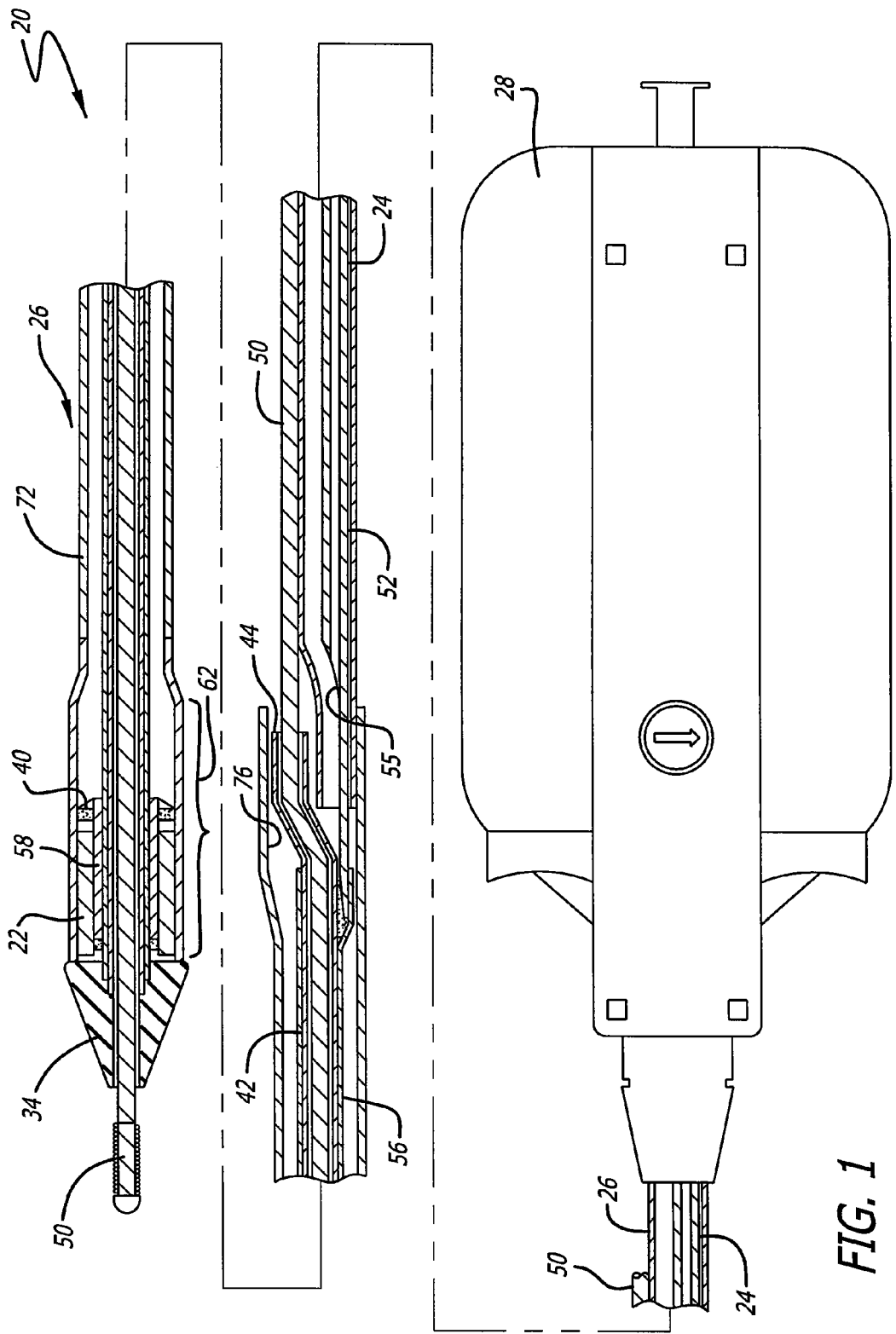
FIG. 1 is a side elevational view, partially in cross section, showing a rapid-exchange stent delivery system embodying features of the present invention.

In one embodiment of the invention, as exemplified in FIG. 1, a rapid-exchange catheter assembly 20 is provided to deliver and implant a stent 22. Rapid-exchange catheters are known in the art and details of the construction and examples of use are set forth in U.S. Pat. Nos. 5,458,613; 5,346,505; and 5,300,085. Rapid-exchange catheter assembly 20 incorporates an inner catheter member 24 and an outer catheter member 26. Outer member 26 is slidably positioned over inner member 24 and relative axial movement between the two members is provided by a control handle 28. The control handle 28 can take numerous forms, but is depicted schematically for ease of illustration. As an example, however, control handle can take the form of a thumb-switch arrangement, a rotating-screw-type arrangement, or a ratcheting arrangement. Such control handles are well known in prior art catheter-delivery systems. A suitable control handle which can be used in accordance with the present invention is disclosed in U.S. Pat. No. 6,375,676, which is herein incorporated by reference.

Referring specifically now to FIGS. 1-3, the inner member 24 is shown made from various components which form a composite assembly. The inner member 24 includes a proximal end 30 which is housed within the control handle 28 and a distal end 32 attached to an obturator 34 that is designed to help prevent a snow-plowing effect as the rapid-exchange catheter assembly 20 is delivered through the patient's vasculature. The inner member 24 further includes a distal portion 36 which includes a stent holder 38 utilized for mounting the stent 22 thereon. In this manner, a self-expanding stent 22 may be placed in a compressed state at the stent holder 38 and held in place by the outer member 26. A block element 40 is associated with the stent holder 38 to prevent proximal movement of the stent 22 relative to the inner member 24 as the outer member 26 is retracted proximally to uncover the stent for deployment. This block element 40 also may act as a radiopaque marker to provide enhanced visualization to the physician when utilizing visualization equipment such as a fluoroscope.

The inner member 24 also includes a guide wire receiving member 42 which defines a lumen and is configured to extend from a proximal end 44 to a distal end 46 located in the region of the distal portion 36 of the inner member 24. The profile of this guide wire receiving member 42 extends distally along and adjacent to the catheter and then deflects from being adjacent to the catheter so that it extends coaxially therewith. The guide wire receiving member 42 terminates in a distal opening 48 at its distal end 46. As is shown in FIG. 1, a guide wire 50 is adapted to extend through this guide wire receiving member 42 utilizing "rapid-exchange" technology. In this regard, only a short portion of the guide wire receiving member 42 is necessary in order to steer the composite rapid-exchange catheter assembly 20 through the sometimes tortuous anatomy of the patient's vasculature.

The inner member 24 further includes a substantially long proximal portion 52 made from a tubular member which is attached to the guide wire receiving member 42 and extends to the proximal end 30. This particular proximal portion can be a support hypotube made from, for example, stainless steel or nickel-titanium alloy, which provides support for the rapid-exchange catheter assembly 20 as well as providing compression and kink resistance to the overall catheter assembly 20. The proximal portion 52 creates a passage to allow a flushing fluid to be introduced into the catheter assembly in order to flush the catheter of unwanted air bubbles. A syringe or similar fluid introducing device can be attached to the luer fitting located on the control handle 28 which allows the flushing fluid to be introduced into the catheter assembly to flush air bubbles from the system. This proximal portion 52 provides a semi-rigid tubular column which creates a reduced profile to allow the composite catheter assembly 20 to reach smaller diameter locations in the patient's vasculature while minimizing the chance for compressive or tensile failures during deployment. As can be seen best in FIG. 3, the proximal portion 52, is cut or notched 55 proximal to the proximal opening 54 of the guide wire receiving member 42 with the proximal end 44 being attached to a portion of the guide wire receiving member 42. Suitable adhesives such as 411 Loctite or other compounds can be utilized to attach the proximal portion 52 to the guide wire receiving member 42.

Referring still to FIG. 3, the distal portion 36 of the inner member 24 can be made from multiple layers of materials to form a composite unit. As is shown in FIG. 3, the guide wire receiving member 42 extends distally from its proximal end 44 and can be coaxially encapsulated by a tubular component 56 which can be made from a material such as Nylon 12 or other suitable materials known in the art. A third tubular member 58 which forms part of the stent holder 38 can encapsulate the distal most portion of this second layer 56 and can be made from a relatively softer material, such as Pebax 63D. This particular layer helps to form a support and mounting medium for mounting the self-expanding stent thereto.

Referring to FIGS. 1 and 2, the outer member 26 is configured to surround the inner member 24 and may have a larger diameter at its distal region 60 than at its proximal region in order to accommodate all of the elements of the inner member. The self-expanding stent 22 in its compressed state is positioned on the stent holder 38 of the inner member 24 and is held in compressed state by a restraining sheath portion 62 which forms part of the outer member 26. When the outer member 26 is withdrawn proximally relative to the inner member, the stent 22 is permitted to assume its expanded state so as to support the body lumen within which it is implanted.

Referring still to FIGS. 1 and 2, the outer member 26 is shown made up of various sections which create a composite assembly. The outer member 26 includes a proximal outer member 64 which has a proximal end 66 designed to be attached to the control handle 28. As can be seen in FIG. 1, this proximal outer member 64 is designed to extend coaxially over the proximal portion 52 which forms part of the inner member 24. The distal end 68 of this proximal outer member 64 tapers at a point where the distal end of the guide wire receiving member 42 would be placed when the inner and outer members are assembled together. As is best seen in FIG. 2, the proximal outer member 64 tapers down to a smaller lumen 70 which terminates proximal of the attachment point between the proximal end of the support tubing with the guide wire receiving member 42.

The outer member 26 further includes an intermediate portion 72 which extends from a proximal end 74 where it is bonded utilizing laser, heat or adhesive to the distal end 68 of the proximal outer member 64. In this regard, the intermediate portion 72 has a larger diameter than the much smaller diameter tapered region formed at the distal most end of the proximal outer member 64. This intermediate portion 72 can be made from a strong but flexible material, such as Nylon 12, and extends distally and is attached to the distal restraining sheath portion 62 which is adapted to extend over the compressed stent 22 to maintain it in a collapsed position until the stent is ready to be deployed. As can be best seen in FIG. 2, this distal sheath portion 62 has a somewhat larger diameter than the diameter of the intermediate portion 72 in order to be disposed over the stent holder and the collapsed stent. For example, this distal sheath portion 62 can be made from materials such as a Pebax-coated polymide or a Nylon-coated polymide which will be described in greater detail below.

As can be best seen in FIG. 1, the proximal end 44 of the guide wire receiving member 42 is designed to extend between a space 76 formed between the proximal outer member 64 and the intermediate portion 72. In this regard, when the outer member 26 is retracted proximally via the control handle 28, the guide wire receiving member 42 remains unattached to the intermediate portion 72 which will move back proximally. As a result, the guide wire receiving member 42 remains independent from the outer member 26 to allow the outer member 26 to move freely in an axial direction to either cover or uncover the stent 22.

Referring now to FIGS. 4-8, another embodiment of a rapid-exchange catheter assembly 80 incorporating features of the present invention is shown. In this particular embodiment of the invention, there are a number of similar components which are common to the embodiment of the rapid-exchange catheter assembly 20 shown in FIGS. 1-3. One of the differences in the embodiment of the invention shown in FIGS. 4-8, however, is that the proximal portion of the inner member is not made from a tubular member, such as a hypertube but, rather, is replaced by a support mandrel 82 that includes a proximal end 84 connected to the control handle 28 and a distal end 86 connected to a guide wire receiving member. The guide wire rapid-exchange catheter assembly 80 also includes a similar outer member 88 coaxially disposed over an inner member 90. Referring initially to the inner member 90, the arrangement of components includes a stent holder 92 and an obturator 94 which, again, is used to prevent a "snow-plowing" effect as the catheter assembly 80 is moved within the patient's vasculature. The guide wire receiving member 94 includes a proximal opening 96 and a distal opening 98 which creates a small conduit utilized to deliver the catheter assembly 80 over a pre-deployed guide wire (not shown). This inner member 90 functions in the same fashion as the previously described inner member 24 of the rapid-exchange catheter assembly 20 shown in FIGS. 1-3. Again, the major difference is the inclusion of a support mandrel 82, rather than a hypotube, which forms the proximal portion of the inner member 90. The use of such a mandrel may allow for a lower delivery profile and may provide additional axial stiffness to the catheter assembly as the assembly is being pushed through the patient's anatomy.

The outer member 88 of the rapid-exchange catheter assembly 80 is made up of several portions or sections which provide different functions. As is shown in FIGS. 4 and 5, the outer member 88 includes a proximal portion 100 having a proximal end 102 and a distal end 104. This particular proximal portion 100 can be a tubular component which allows the proximal end 102 to be attached to the locking handle 28 which actuates the retraction of the outer member 88. The distal end 104 is, in turn, attached to an intermediate portion 106 which extends distally to a third section, namely, the restraining sheath portion 108 that is adapted to maintain the stent 22 in a collapsed position until it is ready to be deployed in the patient's vasculature. This intermediate portion 106 has a proximal end 110 attached to the distal end 104 of the proximal portion 100. The intermediate portion 106 also includes a distal end 112 attached to a proximal end 114 of the sheath portion 108. These particular components can be attached together utilizing laser, heat, or adhesive bonding techniques well known in the art.

Referring initially to the proximal portion 100 of the outer member 88, the material and shape of the component forming this section of the outer member 88 can be made from a single lumen tubing, using catheter material well known in the art. The intermediate portion 108 is made from a tubular member having a pair of lumens extending therethrough. In the embodiment of FIGS. 4-8, the intermediate portion 106 has double D lumen which creates a first channel or lumen 116 through which the support mandrel 82 is designed to extend therethrough and a second channel or lumen 118 used to create a guide wire exit notch 120 that allows for positioning the movement of the guide wire receiving member 42 during deployment. FIG. 8 shows a cross sectional view at the bonding region of the proximal portion 100 and intermediate portion 106 and shows the two separate channels 116 and 118 which are formed in the intermediate portion 106.

The guide wire notch 120 (FIG. 7) creates an opening to allow a guide wire to extend therethrough in the guide wire receiving member 42 formed on the inner member 90. During use, the proximal end of the guide wire receiving member 42 is allowed to extend through and move axially through this second channel 118 which remains distal of the guide wire notch 120 formed in the second channel 1118. FIG. 6 shows the cross-sectional arrangement of the guide wire receiving member 42 as it extends within the second channel 118 formed on the intermediary portion 106.

Referring now to FIGS. 9 and 10, an alternative embodiment of an inner member 130 which can be used in accordance with the present invention is disclosed. For sake of clarity, FIGS. 9 and 10 do not show an outer member which would be utilized in conjunction with this inner member 130 to form a composite rapid-exchange catheter assembly. In this particular embodiment, the inner member 130 utilizes a proximal portion 132 which can be made from a tubular component such as a hypotube, as was previously disclosed in the embodiment of FIGS. 1-3. The proximal portion 132 includes a proximal end 134 attached to the control handle (not shown) and a distal end 136 attached to a distal portion 138 of the inner member 130. In this particular embodiment, the distal portion 138 is different from the previously disclosed embodiments in that the guide wire receiving member 140 is formed from a tubular material which includes a wire coil 142 encapsulated by a polymeric material, such as Pebax. As can be seen best in FIG. 10, the proximal portion 132 includes a notched region 144 which creates an opening through which a guide wire (not shown) can extend through. A second layer 146, which encapsulated at least a portion of the guide wire receiving member 140, could be made from a tubular material. In one aspect, the second layer 146 can be made from Nylon or similar material. Accordingly, a stent holder 146 is created between a marker band 150 which can be made from a highly radiopaque material, such as tantalum, and provides an abutting shoulder that helps to prevent the stent (not shown) from retracting proximally as the outer restraining sheath is retracted to expose the stent for deployment. An obturator 152 can be attached to an inner member 130.

The use of a coil tubing to form the guide wire receiving member helps to prevent compressibility of the inner member without decreasing the flexibility of the catheter assembly. Thus, in use, the guide wire receiving member will support the direct amount of compression force that is placed on the inner member during deployment, preventing the inner member from compressing and providing accurate stent placement. Such a guide wire receiving member is valuable in situations in which high deployment forces can be developed during deployment. In other words, the higher the deployment force, the more the inner member will compress during deployment. As the diameters of the self-expanding stents increase, along with increased radial strength, a guide wire receiving member which utilizes a coil tubing should help to provide accurate stent placement and absorb the compression exerted on the assembly. Such a guide wire receiving member would still provide increased flexibility and trackability at the distal portion of the catheter assembly as it is delivered through tortuous anatomy.

In the particular embodiment shown in FIGS. 9 and 10, the guide wire receiving member is made from a coil which is coated with a polymeric material, such as Pebax. The intent of the use of a Pebax coating is to allow the wire coil to be easily heat bonded to other components of the inner member. Although the coil is shown coated with a polymeric material, such as Pebax, it should be noted that other similar materials could be utilized as well. Alternatively, a wire coil tubing, without a coating could possibly be utilized in creating the guide wire receiving member as well.

Referring now to FIGS. 11 and 12, yet another embodiment of an inner member 160 made in accordance with the present invention is shown. In this particular embodiment of the invention, the inner member 160 is shown including a proximal portion 162 made from a wire coil tubing, such as a tubing described above, and utilized to form the guide wire receiving member in the embodiment of FIGS. 9 and 10. In this particular embodiment, the proximal portion 162 has a proximal end 164 attached to the control handle 28 and a distal end 166 which extends into the stent holder 168 formed at the distal end of the inner member. A guide wire receiving member 170 also is attached to the proximal portion 162. A portion of the proximal portion and the guide wire receiving member 170 can be bonded together by an encapsulating layer 172 formed in the region of the stent holder 168. Flush holes 174 which extend into the surface of the stent holder 168 and encapsulating layer 172 allow for ease of flushing a fluid through the coil tubing to purge the catheter of air bubbles. The layer 172 can be made from a material such as Nylon or a similar polymeric material. The coil tubing which can be utilized to create the proximal portion 162 is similar to the coil tubing 142 utilized to form the guide wire receiving member 140 of the inner member 130 of FIGS. 9 and 10. Again, the coil tubing can be coated with a polymeric material, such as Pebex or similar polymeric material, to create an encapsulated tubing with a lumen extending there through to allow fluid to be introduced into the inner member to purge the composite assembly of any air bubbles. Again, as with the inner member 130 shown in FIGS. 9 and 10, the drawings in FIGS. 11 and 12 do not show the outer member which would be utilized to create the composite catheter assembly.

Referring now to FIGS. 13A-15B, an alternative design for an outer member 180 and inner member 182 made in accordance with the present invention is shown. These figures are intended to show a representative distal end portion of a composite catheter assembly which provides a guide wire exit opening 184 which is utilized to create the rapid exchange portion of the catheter assembly. The guide wire (not shown in FIG. 13A) is designed to extend into an internal lumen formed in the distal portion 183 which is attached to a restraining sheath portion 185. Initially referring to FIGS. 13A and 13B, the outer member 180 is shown including a anti-rotation member 186 formed adjacent to the guide wire exit opening 184. This anti-rotation member is designed to assume a shape which is similar to a lumen shape formed on the inner member 182. It should be remembered that for rapid-exchange catheter assemblies the inner member 182 and outer member 180 should move independent of each other, otherwise the outer member will be unable to retract proximally to deploy the self-expanding stent. While axial motion between the inner and outer members 180 and 182 is desirable, rotational motion between these components can result in undesirable misalignment of the guide wire exit notch formed within the inner and outer member. As a result, it is important to maintain the guide wire exit alignment between the inner and outer members for most rapid-exchange self-expanding stent systems. However, any design which prevents rotational motion between the inner and outer member should not affect the axial motion between members.

Referring now specifically to FIGS. 14A and 14B, the inner member 182 is shown with a proximal portion 188, made from a tubing such as hypotubing, with a taper at the distal end 190. The inner member includes a notched portion 192 formed on the proximal portion 188 and has a general U-shape lumen 194 for the guide wire to sit inside the lumen. The proximal portion 188 is attached to a guide wire receiving member 196 which extends through a stent holder 198 and obturator 200. While the inner member has a generally U-shaped configuration for the guide wire to sit in, it is to be understood that other suitable shapes which allow the guide wire to sit within the lumen could also be utilized in conjunction with the present invention. As is shown in FIGS. 15A and 15B, the inner member 182 is shown placed within the outer member 180 in a coaxial arrangement. In this regard, the anti-rotation member 186 of the outer member is formed in a U-shape and sits within the U-shaped lumen 190 of the inner member to keep the members aligned. The U-shaped anti-rotation member 186 slides within the U-shaped lumen 190 in order to affect axial movement between the inner and outer members, however, the anti-rotation member 186 prevents any rotational motion between these two members, since the similar U-shape of the anti-rotation member 186 basically encapsulates the U-shaped lumen 190 of the inner member 182 preventing any rotational movement, at least within the guide wire exit opening 184. The guide wire 202 normally will not move as the outer member 180 is retracted relative to the inner member 182.

Generally, the guide wire exit opening 184 is formed on the outer member by piercing the tubular material forming the outer member with a mandrel for initially forming the guide wire exit opening. In this regard, a guide wire which is larger than the diameter of the guide wire utilized with the rapid-exchange catheter assembly is used to create a notch within the outer member. The mandrel can be heated and pressed down onto the outer member to form the U-shaped anti-rotation member 186 adapted to the guide wire exit opening. Again, this U-shaped member should match the same shape as the U-shaped lumen 190 formed on the inner member. With both the inner and outer member retaining the same U-shaped configuration, the two members will align together and slide axial to each other without independent rotation. The axial movement between the inner and outer members at the guide wire junction should not affect the positioning of the guide wire 202 within the guide wire exit notch since the inner and outer member will not rotate to misalign the respective notches formed therein. It should be appreciated to those skilled in the art that other methods for forming the U-shape on the anti-rotation member can be implemented without departing from the spirit and the scope of the present invention. Also, as mentioned above, the anti-rotation member and the lumen of the inner member can be formed in shapes other than a U-shape.

Figure 16:
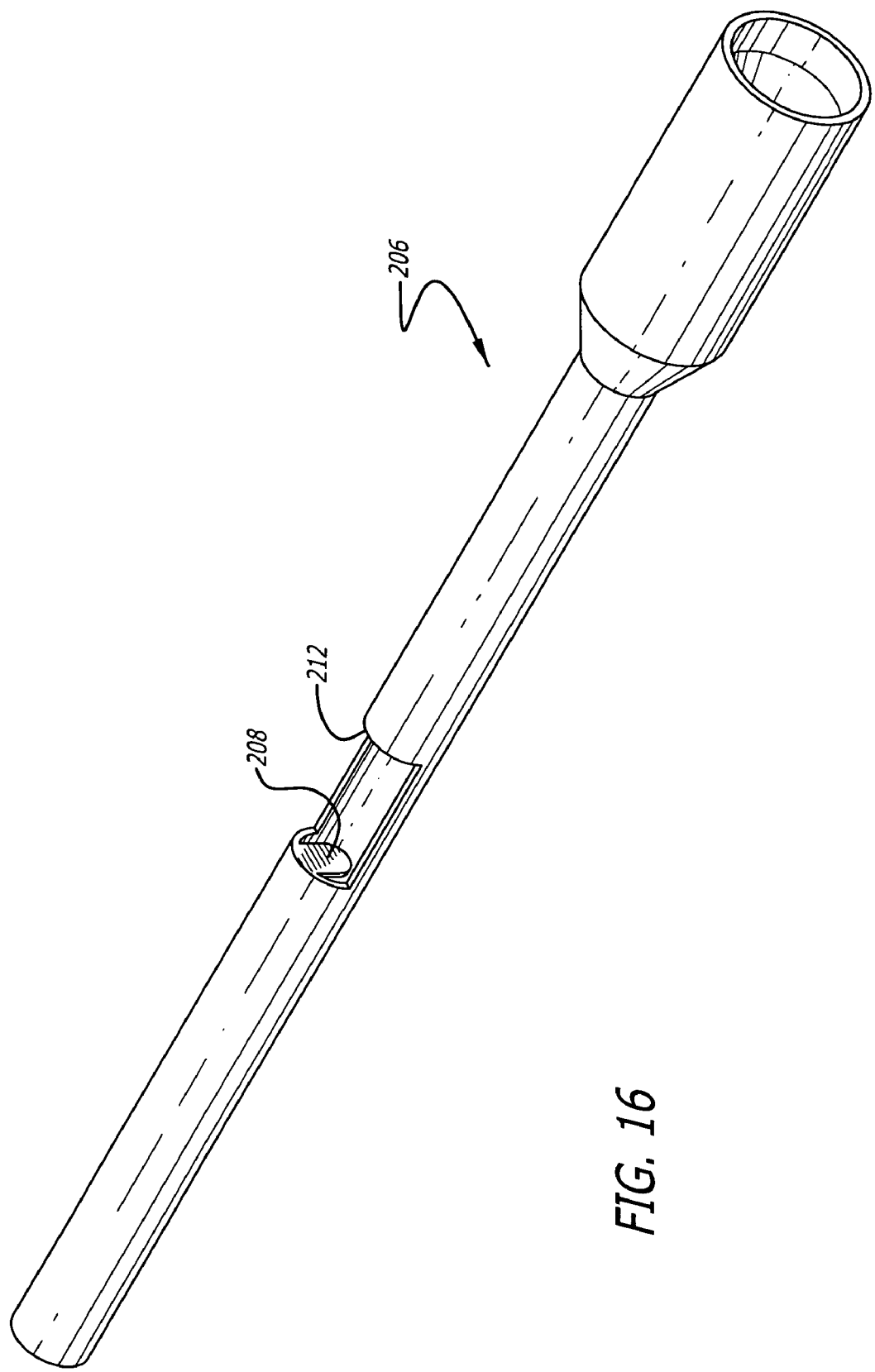
FIG. 16 is a perspective view showing an alternative embodiment of a distal portion of an outer member which forms part of a rapid-exchange stent delivery system embodying features of the present invention.
Figures 17A, 17B:
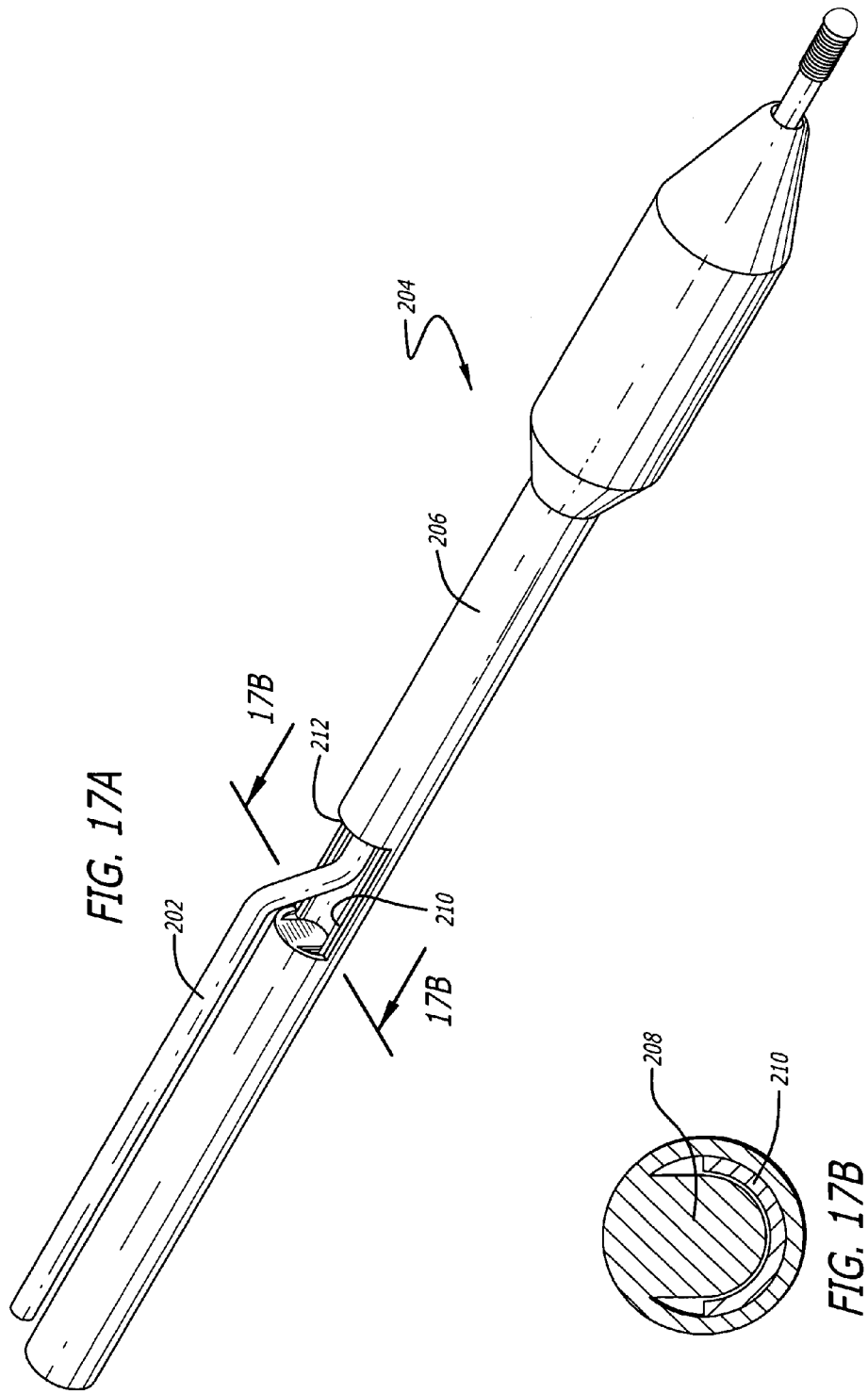
FIG. 17A is a perspective view showing the complete distal junction assembly, which includes the outer member of FIG. 16 and the inner member of FIG. 14A.
FIG. 17B is a cross sectional view taken along line 17B-17B of FIG. 17A.

Referring now to FIGS. 16-17B, an alternative catheter assembly 204 is disclosed. This particular assembly is similar to the one shown in FIGS. 13A-15B except the means for preventing rotation which is formed on the outer member 206 differs somewhat from the previously disclosed embodiment. An inner member, such as the one shown in FIGS. 14A and 14B, can be utilized in conjunction with this particular embodiment as well. As can be seen best in FIG. 16, the outer member 206 includes a tab-like projection or member 208 which extends into the inner lumen formed in the outer member 194. This tab-like member 208 has a generally U-shape and is designed to sit within the U-shaped lumen 210 which is formed in the inner member. This U-shaped, tab-like member 208 functions similarly as to the U-shaped anti rotation member 186 used in the previously described embodiment in that axial movement between the inner member and outer member can be achieved while preventing rotational motion between these two members. FIGS. 17A and 17B show the arrangement of the outer member 206 and the inner member utilizing this tab-like member 208. This shows just one particular shape which can be utilized in order to prevent rotational motion between the inner and outer members at the guide wire exit opening 212. It is to be understood that variations as to the size, location and shape of this tab-like member 208 could be implemented without departing from the spirit and scope of the present invention.

Figure 19:
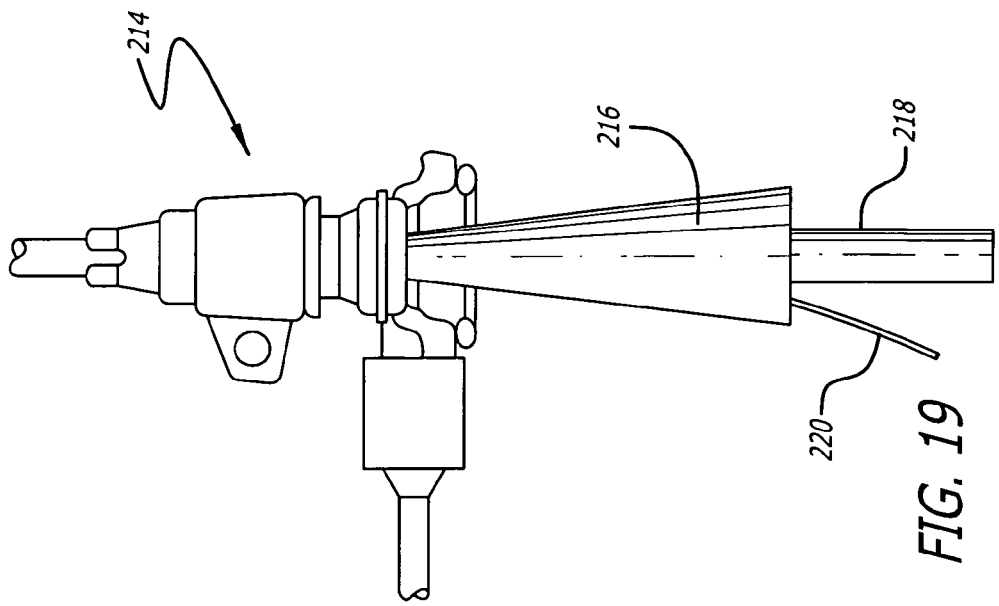
FIG. 19 is a side elevational view, partially in cross section, showing an alternative use of a funnel component which can be utilized in conjunction with a rotating hemostatic valve.
Figure 18:
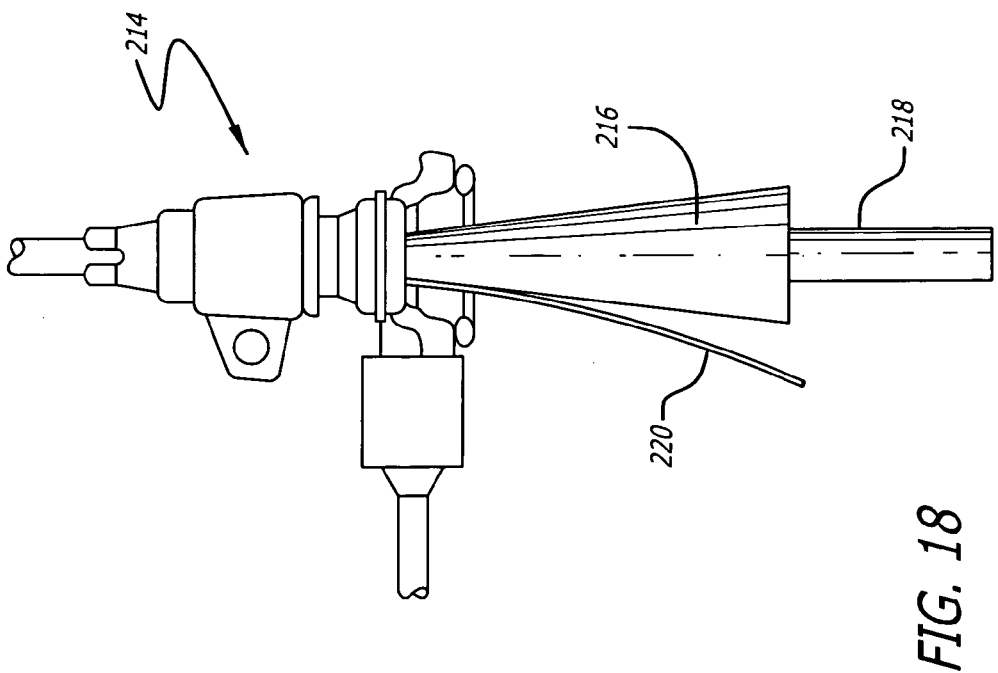
FIG. 18 is a side elevational view, partially in cross section, showing a funnel component which can be utilized in conjunction with a rotating hemostat valve.

Referring now to FIGS. 18 and 19, a schematic representation of a hemostasis valve 214 is shown with a funnel introducer 216 utilized to relieve pressure which may be exerted on a catheter assembly 218 that may be placed within the hemostasis valve 214. The introduction of catheters into blood vessels for a variety of purposes, such as coronary angiography and angioplasty, has been known for many years. Techniques for introducing these catheters into the vasculature into the human body are well known. One such technique utilizes the surgical insertion of a needle into a vein or artery utilizing a sheath which usually includes a hemostasis valve that inhibits blood loss as the guide wires, catheters and the like are introduced, passed through and manipulated in the introducer sheath. A hemostasis valve provides a fluid-tight seal at all times to prevent back-bleeding and usually offers relatively low friction when the intravascular devices are inserted therein. For most self-expanding stent catheter assemblies, an outer member moves proximal when deployed, which motion can be hindered when clamped within the opening of the hemostasis valve. Particularly, for a rapid-exchange self-expanding system, the outer member along with the guide wire are usually pinched between the hemostasis valve. During deployment, as the outer member moves proximally, the guide wire can be dragged proximal as well due to the tight fit at the hemostasis valve. As a result, there is a possible effect of deployment accuracy due to the friction developed between the outer member and the hemostasis valve during deployment, along with possible movement of the guide wire during stent deployment. Whenever a self-expanding stent is utilized with such a hemostatic valve, any movement of the guide wire and/or catheter assembly can be critical to the accurate deployment of the stent within the patient's vasculature.

The purpose of the funnel introducer 216 in conjunction with the hemostatic valve 214 is to relieve the pressure which may be exerted on the outer member 218 and guide wire 220. As is shown in FIGS. 18 and 19, the introduction of the funnel introducer 216 into the hemostasis valve 214 allows the particular stent delivery system to be advanced with little force and friction caused by the hemostasis valve itself. For rapid-exchange self-expanding delivery systems, the guide wire 220 can be placed within the funnel introducer 216, as is shown in FIG. 19, or it can be placed outside the funnel introducer as is shown in FIG. 18. When placed within the funnel introducer 216, as shown in FIG. 18, the guide wire 220 is pinched between the funnel introducer 216 and the hemostasis valve 214 and does not make in contact with the catheter assembly 218 as it moves proximally during deployment. As a result, the possibility that the guide wire 220 will move in response to movement of the outer member of the catheter assembly is minimized. Additionally, when the guide wire 220 is placed within the funnel introducer 216, as is shown in FIG. 19, movement of the guide wire is somewhat minimized while the pinching effect on the outer member should be minimized.

The stent as described herein can be formed from any number of materials, including metals, metal alloys and polymeric materials. Preferably, the stent may be formed from metal alloys such as stainless steel, tantalum, or the so-called heat sensitive metal alloys such as nickel titanium (NiTi). Stents formed from stainless steel or similar alloys typically are designed, such as in a helical coil or the like, so that they are spring biased outwardly.

With respect to all of the embodiments disclosed above, some of the components of inner member and outer member can be formed from stainless steel or nickel-titanium hypotube, as noted above, or polymeric materials including polyethylenes, polyethylterpthalates, nylons, polyurethanes, elastomeric polyesters and the like. Generally speaking, the more proximal portions of inner member and outer member can be formed from material that is stiffer than the distal section so that the proximal section has sufficient pushability to advance through the patient's vascular system. On the other hand, the more distal portion of inner member and outer member can be formed of a more flexible material so that the distal portion of the catheter will remain flexible and track more easily over the guide wire.

The distal portion of the outer member which forms the restraining sheath portion of any of the embodiments of the self-expanding stent delivery system can be made with a Nylon-coated polyimide material that provides high-strength tubing, with a low-wall thickness. Such a material can resist an equal amount of hoop stress at a much lower wall thickness than with a Nylon material alone. In one component, a nylon material is bonded to the outside of a polyimide tubing. The inner surface of the polyimide tubing remains resistant to stent-strut indentation caused by the outward radial force exerted by the collapsed self-expanding stent. The Nylon material bonded to the outside of the sheath provides the necessary tubing strength to restrain the stent in a collapsed delivery position, but with a lower wall thickness. As a result, the profile of the stent delivery system can be reduced at its distal region by utilizing such a composite material.

Other modifications and improvements may be made without departing from the scope of the invention. For example, the leaf spring is not limited to the shape exemplified in the drawings, but may be any expanding member and may assume any shape which expands to protrude through an opening or slot in the outer member. Accordingly, it is not intended that the invention be limited, except as by the appended claims.

What is claimed is:

1. A catheter assembly comprising:
   a control handle;
   an inner catheter member having a proximal end and a distal end and further including a distal mounting portion adapted to have a medical device mounted thereon, the proximal end attached to the control handle, and a guide wire receiving member having a proximal end and a distal end and being configured for receiving a guide wire, the proximal end of the guide wire receiving member being spaced apart from the proximal end of the inner catheter member, the guide wire receiving member further including an opening at the proximal end and an opening at the distal end and a lumen extending between these openings formed on the distal and proximal ends of the guide wire receiving member; and
   an outer catheter member co-axially disposed over the inner catheter member and dimensioned for relative axial movement relative to each other, the outer catheter member being comprised of multiple portions, wherein the outer catheter member includes a distal portion having a proximal end and a distal end, the distal portion being adapted to at least partially cover the medical device, the distal portion having an inner surface configured to directly contact the medical device, an intermediate portion having a distal end and a proximal end, the distal end of the intermediate portion coupled to the proximal end of the distal portion, and a proximal outer member having a proximal end and a distal end, the proximal end of the proximal outer member being coupled to the control handle and the distal end of the proximal outer portion being coupled to the proximal end of the intermediate portion, wherein the proximal end of the intermediate portion has an outer diameter and the distal end of the proximal outer member has an outer diameter, the outer diameter of the proximal end of the intermediate portion being larger than the outer diameter of the distal end of the proximal outer member to allow for a guide wire to exit the proximal end of the guide wire receiving member through an opening formed at the proximal end of the intermediate portion of the outer catheter member, wherein a length of the proximal portion extends into the opening of the proximal end of the intermediate portion to create a passage between the proximal portion and the intermediate portion through which the guide wire is configured to extend.

2. The catheter assembly of claim 1, wherein the intermediate portion of the outer catheter member includes a lumen and the proximal end of the guide wire receiving member is slidably disposed within this lumen.

3. The catheter assembly of claim 2 wherein the distal mounting portion of the inner catheter member has a lumen extending therethrough and a portion of the guide wire member extends through this lumen.

4. The catheter assembly of claim 3 wherein the portion of the guide wire receiving member extending through the lumen of the distal mounting portion is secured to the wall forming the lumen.

5. The catheter assembly of claim 3 wherein the portion of the guide wire receiving member which does not extend through the lumen of the distal mounting portion is slidably disposed within the lumen of the intermediate portion of the outer catheter member.

6. The catheter assembly of claim 2 wherein a portion of the guide wire receiving member is housed in the lumen of the intermediate portion.

7. The catheter assembly of claim 1 wherein the intermediate portion of the outer catheter member is made from a material which is more flexible than the material forming the proximal portion of the outer catheter member.

8. The catheter assembly of claim 1 wherein the proximal portion of the inner catheter member is made from a hypotube.

9. The catheter assembly of claim 1 wherein the proximal end of the guide wire receiving member is located within the passage.

10. The catheter assembly of claim 9 wherein the proximal end of the guide wire receiving member is slidably disposed within the passage of the outer catheter member.

11. A catheter assembly comprising:
    a control handle;
    a medical device;
    an inner catheter member having a proximal end and a distal end and further including a distal mounting portion upon which the medical device is mounted, the proximal end being coupled to the control handle, a guide wire receiving member for receiving a guide wire, the guide wire receiving member having a proximal end, a distal end and a lumen for receiving the guide wire, the proximal end of the guide wire receiving member being spaced apart from the proximal end of the inner catheter; and
    an outer catheter member coupled to the control handle and co-axially disposed over the inner catheter member and dimensioned for relative axial movement relative to each other, the outer catheter member comprising:
    a distal portion having a proximal end, a distal end and lumen extending therethrough, the distal portion being adapted to at least partially cover the medical device and having an inner surface which directly contacts the medical device;
    an intermediate portion made from a tubular member having a proximal end, a distal end and a lumen extending therethrough, the proximal end of the distal portion being coupled to the distal end of the intermediate portion;
    a proximal portion made from a tubular member having a proximal end and a distal end, the proximal end of the intermediate portion having an opening that is greater than the diameter of the distal end of the proximal portion, the distal end of the proximal portion being attached within the proximal end of the intermediate portion such that a length of the proximal portion extends into the opening of the proximal end of the intermediate portion; and a passage formed between the proximal portion and the intermediate portion at the area of attachment, the passage allowing for a guide wire to pass through the opening of the intermediate portion to exit the lumen of the guide wire receiving member.

12. The catheter assembly of claim 11 wherein the proximal end of the guide wire receiving member has an opening to the lumen of the guide wire receiving member and the proximal end of the guide wire receiving member extends into the passage formed on the outer catheter member.

13. The catheter assembly of claim 11 wherein the distal mounting portion includes a tubular member having a proximal end and a distal end and a lumen extending therethrough.

14. The catheter assembly of claim 13 wherein at least a portion of the guide wire receiving member extends through the lumen of tubular member of the distal mounting portion.

15. The catheter assembly of claim 14 wherein the inner catheter member includes a proximal portion having a proximal end and a distal end, the distal end of the proximal portion being coupled to the tubular member of the distal mounting portion.

16. The catheter assembly of claim 15 wherein the proximal portion of the inner catheter member is an elongate component.

17. The catheter assembly of claim 16 wherein the elongate component is a length of hypotube.

18. The catheter assembly of claim 17 wherein the proximal portion of the outer catheter member includes a lumen and the proximal portion of the inner catheter member extends through this lumen.

19. The catheter assembly of claim 18 wherein the proximal portion of the inner catheter member is slidable within the lumen of the proximal portion of the outer catheter member.

20. The catheter assembly of claim 11 wherein the guide wire receiving member defines a distal portion and a proximal portion, at least a portion of the proximal portion of the guide wire receiving member extending through the lumen of the intermediate member.

21. The catheter assembly of claim 20 wherein the proximal portion of the guide wire receiving member is slidable within the lumen of the intermediate member.

22. The catheter assembly of claim 11 wherein the proximal end of the guide wire receiving member has an opening to the lumen of the guide wire receiving member and the opening of the proximal end of the guide wire receiving member aligns with the passage formed on the outer catheter member.

23. The catheter assembly of claim 22 wherein the guide wire receiving member has a distal portion and a proximal portion, at least a portion of the proximal portion of the guide wire receiving member extending through the lumen of the intermediate member.

24. The catheter assembly of claim 23 wherein the proximal portion of the guide wire receiving member is slidable within the lumen of the intermediate member.

25. The catheter assembly of claim 11 wherein the distal end of the proximal portion extends into and is attached within the lumen of the intermediate portion of the outer catheter member.

26. The catheter assembly of claim 11 wherein the entire length of the proximal portion of the outer catheter has a smaller diameter that the intermediate portion.

27. The catheter assembly of claim 11 wherein the tubular member forming the distal end portion of the proximal portion has a tapered diameter.

28. The catheter assembly of claim 27 wherein the tapered portion of the proximal portion and the proximal end of the intermediate portion cooperate to form the passage for the guide wire.

29. The catheter assembly of claim 28 wherein the proximal end of the guide wire receiving member is bent to fit within the passage formed on the outer catheter member.

30. The catheter assembly of claim 11 wherein the proximal end of the guide wire receiving member is located within the passage.

31. The catheter assembly of claim 30 wherein the proximal end of the guide wire receiving member is slidably disposed within the passage of the outer catheter member.

32. A catheter assembly comprising:

a control handle;

a medical device;

an inner catheter member having a proximal end, a distal end, a distal mounting portion upon which the medical device is mounted and a guide wire receiving member for receiving a guide wire, the proximal end of the inner catheter being coupled to the control handle, the guide wire receiving member having a proximal end, a distal end and a lumen for receiving the guide wire, the proximal end of the guide wire receiving member being spaced apart from the proximal end of the inner catheter; and an outer catheter member coupled to the control handle and co-axially disposed over the inner catheter member and dimensioned for relative axial movement relative to each other, the outer catheter member comprising:

a distal portion having a proximal end, a distal end and lumen extending therethrough, the distal portion being adapted to at least partially cover the medical device and having an inner surface which contacts the medical device;

an intermediate portion made from a tubular member extending from the distal portion, the intermediate portion having a proximal end with an opening, a distal end with an opening and a lumen extending therethrough;

a proximal portion made from a tubular member extending from the intermediate portion, the proximal portion having a proximal end coupled to the control handle and a distal end with an opening, the proximal end of the intermediate portion having a diameter that is greater than the diameter of the distal end of the proximal portion, wherein a length of the proximal portion extends into the opening of the proximal end of the intermediate portion forming a passage, the guide wire receiving member being placed within the passage to allow a guide wire to pass through the guide wire receiving member and through the opening at the proximal end of the intermediate portion.

33. The catheter assembly of claim 32 wherein the passage has a longitudinal length.

34. The catheter assembly of claim 33 wherein the proximal end of the guide wire receiving member is located within the passage.

35. The catheter assembly of claim 34 wherein the outer catheter member is capable of sliding longitudinally relative to the inner catheter member and the passage of the outer catheter slides relative to the proximal end of the guide wire receiving member.

* * * * *